United States Patent [19]

Homsy et al.

[11] 3,992,221
[45] Nov. 16, 1976

[54] METHOD OF TREATING EXTENSIBLE HYDROCARBON ARTICLES

[75] Inventors: Charles Albert Homsy; John Lee Margrave; Ramachandra Brijlal Badachhape, all of Houston, Tex.

[73] Assignee: Vitek, Inc. & MarChem, Inc., Houston, Tex.

[22] Filed: Oct. 23, 1975

[21] Appl. No.: 625,347

[52] U.S. Cl. .................. 134/16; 2/168; 134/21; 134/22 R; 134 29/; 134/30; 134/42; 264/83
[51] Int. Cl.² .................. B08B 7/02; B29D 31/00
[58] Field of Search .............. 134/16, 21, 22 R, 29, 134/30, 31, 42; 264/83, 232, 307; 2/168; 34/36; 21/58

[56] References Cited
UNITED STATES PATENTS

| | | | |
|---|---|---|---|
| 1,994,317 | 3/1935 | Linscott | 264/307 X |
| 2,497,046 | 2/1950 | Kropa | 264/83 X |
| 2,829,070 | 4/1958 | Osborn | 264/83 X |
| 3,424,828 | 1/1969 | Harris et al. | 264/83 |
| 3,626,517 | 12/1971 | Kurtz | 2/168 |
| 3,637,411 | 1/1972 | Agostinelli | 264/307 X |
| 3,862,284 | 1/1975 | Dixon et al. | 264/83 |

Primary Examiner—S. Leon Bashore
Assistant Examiner—Marc L. Caroff
Attorney, Agent, or Firm—Michael P. Breston

[57] ABSTRACT

A method of treating a surface of an extensible hydrocarbon article by positioning the article in a chamber from which extraneous oxidizing agents are excluded, extending the article, and treating the extended surface with a fluorinating gas which may contain elemental fluorine or a mixture of same with an inert gas such as nitrogen. The treatment provides improved frictional characteristics, chemical inertness, and other desirable properties.

11 Claims, 6 Drawing Figures

METHOD OF TREATING EXTENSIBLE HYDROCARBON ARTICLES

BACKGROUND OF THE INVENTION

1. Field of the Invention a. The invention generally relates to a method of treating elastomeric articles made from extensible hydrocarbon materials in order to reduce their surface friction characteristics and improve their chemical inertness.

b. The invention has particular utility for medical articles, such as surgeons' gloves, that require sliding contact with the surface of the elastomer.

2. Description of the Prior Art

Extensible articles made from hydrocarbon elastomers are now in wide use, particularly in the medical field. For example, medical articles such as surgeons' gloves, catheters, condoms, endoscopic tubes, contraceptives such as intrauterine devices, etc., can be made from a latex rubber or other hydrocarbon elastomeric materials. For medical, surgical and other uses, it is frequently required that such flexible articles be disposed in intimate contact with tissue and/or be used in the presence of blood. In some cases, extension of the article may be concomitant with contact with tissue, as is the case, for example, with the inflated segment of a tracheal tube. In many such medical applications, high friction between the extensible or extended article and the adjacent tissue deleteriously affects the physical properties of the article itself and/or creates a source of irritation for the tissue.

While this invention is not limited to any particular extensible article, it will be illustrated with reference to common, but yet relatively complex in shape, articles such as surgeons' gloves.

Prior to donning a pair of conventional gloves, common practice requires that a lubricating agent such as powder be sprayed inside the gloves, or that the surgeon powder his hands. Also in some manufacturing processes a lubricating powder is generously used on the gloves to facilitate their removal from molds or forms. The same powder also subsequently serves as the desired lubricating agent.

It is now widely recognized that the presence of any lubricating powder on surgeons gloves may lead to potential medical complications, as more fully described in an article entitled THE GLOVE STARCH PERITONITIS SYNDROME by Ignatius et al, published in the Annales of Surgery, March, 1972, Vol. 175, No. 3, pages 388–397.

The potential medical complications are generally attributed to the lubricating powder's fine particles eliciting local inflammatory responses in adjoining tissue. Recently the U.S. Food and Drug Administration issued guidelines for surgical practice which encourage the surgeon to wipe his gloved hands thoroughly with a moist sponge prior to performing surgery in order to remove whatever powder may exist on th gloves' outer surfaces. Even if this recommended cleansing treatment were to remove most of the lubricating powder from the gloves' exterior surfaces, a tear in the glove might allow the transfer of powder from the glove's inner surfaces into an adjoining operative site, where the presence of powder might cause tissue inflamation. In addition to the patient's response to the powder, the wearer himself may suffer a dermatologial allergy.

Also, since fine particles of lubricating powder resist being completely washed away from the gloves' surfaces, they maintain the slipperiness of such surfaces. This apparently unavoidable residual lubricating effect of the powder, especially in the presence of blood, hinders the precise manipulation of surgical instruments and tends to reduce the tactile sensation between the surgeon's fingers and such instruments.

Another glove lubricating process is described in U.S. Pat. No. 3,626,517 which involves the development of a lubricating coating on the glove's inside surface. During the donning of a surgeon's glove, its aperture must be stretched substantially in order to allow penetration of the surgeon's hand inside the glove. The aforesaid lubricating coating could easily fracture during distension of the glove, since the coating's stress elongation characteristics are normally substantially less than the stress elongation characteristics of the glove. The fractured coating and its debris can become a source of tissue irritation.

Other extensible elastomeric articles such as catheters are covered with a jelly, instead of a powder or a coating lubricant, to facilitate their insertion through a luminal orifice of a human body. Catheters are commonly used for relief of bladder contents and can reside in place in the body for more than a few hours. In the body, the jelly lubricant coating gradually loses its lubricating properties leading to a gradual irritating interaction between the catheter and the adjacent tissue. Such irritation may reduce the resistance of the body's luminal orifice to the migration of infectious bacteria through the orifice.

Accordingly, it is a broad object of this invention to provide a method for treating extensible elastomeric articles especially those that are suitable for medical use and are required to have low friction surface characteristics.

SUMMARY OF THE INVENTION

The method comprises treating a surface of an extensible hydrocarbon article by stretching the article in a chamber from which extraneous oxidizing agents are excluded. The article is then treated with a fluorinating gas, which could include a mixture of elemental fluorine or a mixture of same with nitrogen, for a predetermined time interval. There is a range of optimum temperatures, times and composition of the fluorinating gas for the particular article being treated.

In a preferred embodiment of this invention for treating surgeons' gloves, each such glove is placed inside a chamber. Nitrogen is admitted into or passed through the chamber for the purpose of purging the space surrounding the exterior of the glove. After this external purging, the glove is purged internally by inflating it with nitrogen several times which has the effect of purging oxygen from the interior of the glove. A fluorinating pressurized gas is then admitted to the interior of the glove for a predetermined time interval and at a suitable treatment temperature. The admitted pressurized fluorinating gas extends the glove by an appreciable amount and simultaneously treats the glove's exposed inner surface. Thus, the fluorine treatment of the glove is carried out while the glove is extended, causing a larger surface of the glove to become exposed to the treating gas.

After such treatment, the interior of the glove is again purged one or more times with nitrogen. The glove is then removed from its chamber and filled with a cleansing solution which also has the effect of neutralizing any fluorine by-products which may have been formed during the treatment process. The cleansing solution may be 0.1N NaOH, or 0.1N Na$_2$CO$_3$ or, similar neutralizing solution to remove HF. The glove is then washed with a suitable solution such as water and then dried.

DETAILED DESCRIPTION OF A PREFERRED EMBODIMENT

Figure 1:
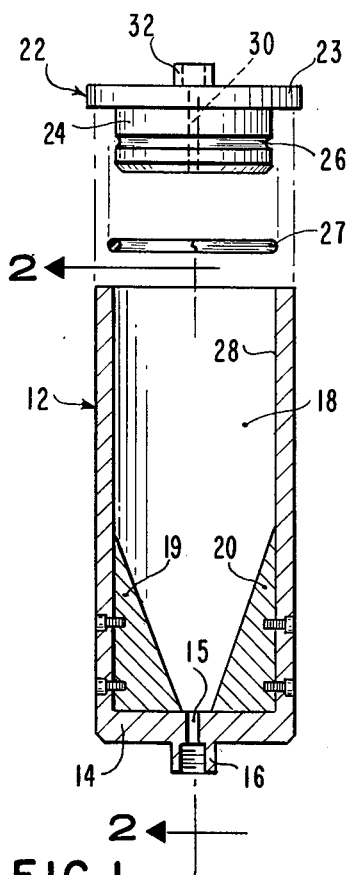
FIG. 1 is a sectional view in elevation of the container used to treat surgeons' gloves.
Figure 3:
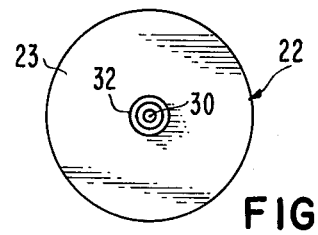
FIG. 3 is a top view of the plug for the container.
Figure 2:
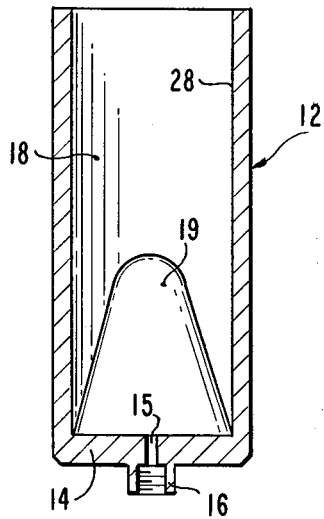
FIG. 2 is a sectional view on line 2—2 in FIG. 1.

Although not limited thereto, the invention will be illustrated in connection with an article having a relatively complex shape, such as a surgeon's glove 10. If when purchased the glove contains on its inner surface a powder or coating lubricant applied either during or after its manufacture, then the glove is first thoroughly washed to remove all traces of the lubricant, and then dried.

The apparatus used to treat each dry glove can assume various configurations. For limited production runs, each glove can be treated individually inside a hollow cylindrical container, generally designated as 12, having a bottom 14 defining an orifice 15 in fluid communication with an outwardly extending nipple 16. The container defines a cylindrical chamber 18 to the bottom end of which are secured two wedge-shaped inserts 19, 20. The geometric configuration of the inserts is determined by the geometry of the articles being treated. For gloves, the inserts are symmetrically positioned relative to a longitudinal axis extending through orifice 15.

Figure 4:
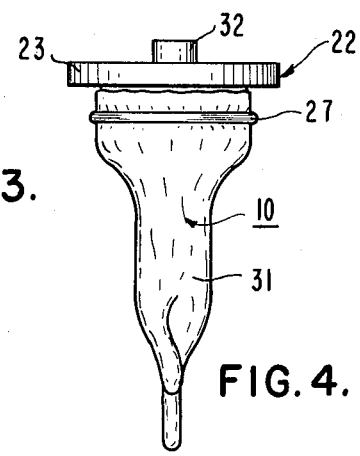
FIG. 4 illustrates the use of the plug to seal the glove's inner space.
Figure 5:
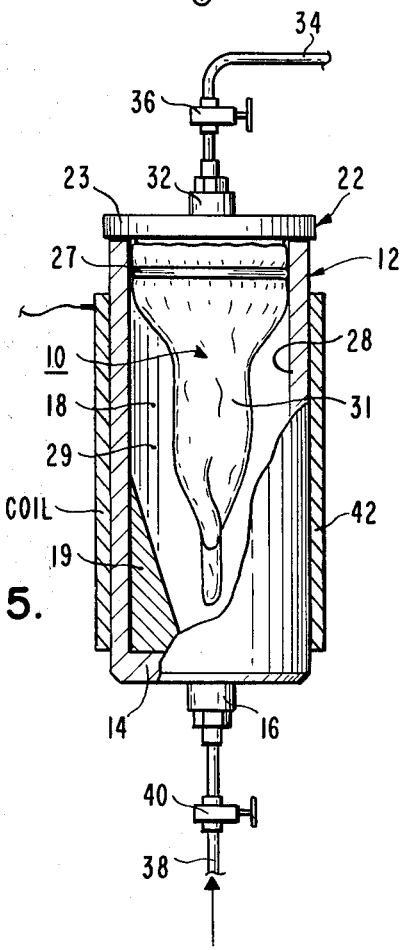
FIG. 5 illustrates the process of heating the container.
Figure 6:
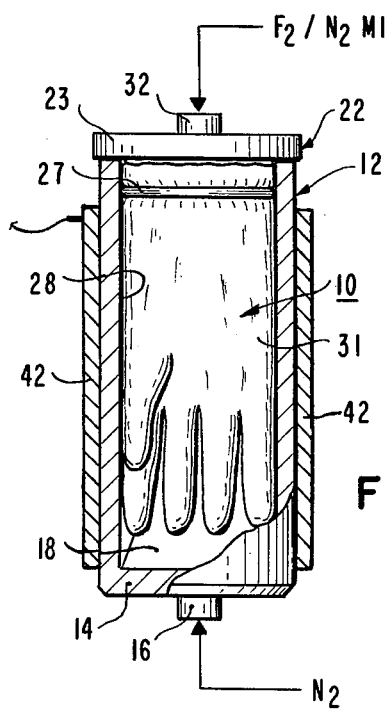
FIG. 6 illustrates the extended condition of the glove inside the chamber.

A plug, generally designated as 22, has a cylindrical head 23 whose outer diameter is slightly larger than the outer diameter of container 12. Extending downwardly from head 23 is a cylindrical glove hanger 24 having an outer diameter slightly less than the inner diameter of chamber 18. A circular groove 26 around hanger 24 accepts therein an O-ring 27 which makes a sealing engagement with the cylindrical inner wall 28 of chamber 18. Plug 22 defines a longitudinal orifice 30 which is in fluid communication between a top nipple 32 and chamber 18. A top fluid lind 34 is connected to the top nipple 32 through a cut-off valve 36. Similarly a bottom fluid line 38 is connected to the bottom nipple 16 through a cut-off valve 40. The glove's cuff is supported by hanger 24 (FIGS. 4–6). The O-ring seals the inner volume of the glove to the cylindrical wall of the hanger.

Container 12 which can be made out of aluminum or stainless steel is heated by a suitable cylindrical electric heating coil 42.

The temperature of the container is regulated by a remotely positioned temperature controller, not shown, actuated by a thermocouple or a bimetallic strip. The function of inserts 19, 20 is to more evenly distribute the heat generated by coil 42 on the glove being treated inside chamber 18. Also, the wall 28 of chamber 18 acts as a limiter for the expansion of the upper portion of the glove (FIG. 6). The dimensions of container 12 and the shape of inserts 19, 20 are selected to ensure that uniform extension of all surfaces of the glove occurs during the fluorinating treatment.

Such treatment will now be described with reference to a presently preferred embodiment of the invention.

After the glove is washed and dried, if needed, as previously described, the cuff of the glove is fitted around hanger 24 and O-ring 27 is rolled over the cuff until it fits inside groove 26. Plug 22 is then positioned over the open end of container 12 leaving an opening therebetween.

Glove Preconditioning

The volume 29 between the exterior wall 31 of the glove and the inner wall 28 of chamber 18 is conditioned with an inert gas consisting of nitrogen, helium, or argon so that oxygen or any other competing oxidizing agents may be excluded from volume 29. Nitrogen is admitted through line 38 and flows out through the top opening of chamber 18 since plug 22 does not then completely seal it. The nitrogen flow rate can be about 100 ml/min for 3 minutes.

Then plug 22 is fully inserted thereby sealing chamber 18. Nitrogen is now admitted through line 34 into the inside of the glove, say at a rate of 600 ml/min for one minute. The nitrogen is then released and re-admitted as many times as may be required to fully purge all the oxygen from the interior space of the glove. Thereafter, only nitrogen will be on both sides of the glove's wall so that no diffusion of oxygen can take place through the glove. After the glove is thusly preconditioned, it is ready to be treated.

Glove Conditioning

A pressurized fluorinating gas which may contain elemental fluorine or a mixture of fluorine with an inert gas consisting of nitrogen, helium, argon, etc., is admitted by line 34 through valve 36 inside glove 10. The fluorinating gas causes the glove to extend by at least 10% which corresponds to a distension that is greater than that which is normally produced by the insertion of the surgeon's hand inside the glove.

The volumetric composition ratio of the fluorinating gas mixture can be between one part fluorine to 20 parts of nitrogen (1:20) and 5 parts of fluorine to one part of nitrogen (5:1). Generally, the richer the mixture is in fluorine the faster the glove's treatment will be and the lower the optimum temperature of treatment is. For example, for a fluorine to nitrogen ratio of 1:10, treatment time must be at least 1 hour and treatment temperature at least 40° C. For ratios approaching the upper range of 5:1, the treatment time may be between a few seconds to a few minutes and the temperature of treatment may be as low as 0° C.

In the preferred embodiment the volumetric ratio of fluorine to nitrogen, 1:2, is admitted to the interior of the glove at a rate of 300 ml/min for 3 minutes so that a total of 900 ml of the treating gas is accumulated inside the glove. Then the flow of the treating gas is cut off and the extended glove is exposed to the treating gas for about 15 minutes at a temperature of about 50° C. Under these conditions, the glove's normal relaxed volume (unstretched) was extended by at least 20%.

After the fluorinating gas mixture has been kept inside the glove for the prescribed time interval, it is released and the inside of the glove is purged one or more times with nitrogen applied through line 34 to the inside volume of the glove.

The glove is then removed from the chamber and separated from plug 22. The glove is filled with a suitable cleansing solution such as water containing 0.1 N NaOH which is allowed to remain for about one minute and up to 10 minutes. The cleansing solution has the effect of neutralizing any fluorine by-products, like HF, which may have been formed during the fluorinating treatment stage. Finally the glove is washed with water and dried.

The fluorine treated inner surfaces of the glove have relatively low friction characteristics, while the cuff portion of the glove, fitted around the hanger 24, not having been exposed to the fluorinating gas, retains its relatively high friction characteristic.

It has been shown by the Electron-Spectroscopy-for-Chemical-Analysis (ESCA) technique, that the foregoing fluorine treatment process involves the direct replacement of some or all of the surface hydrogen atoms, that are covalently attached to the carbon skeleton of the hydrocarbon elastomer, with fluorine atoms. Since the electro-negativity and mass of the fluorine atom are greater than those of the hydrogen atom, and since the carbon-fluorine bond is stronger than the carbon-hydrogen bond, there is obtained a reduction in the glove's critical surface tension and a densification of the treated surface without a detrimental effect on is extensibility.

Gloves treated in accordance with this invention have physical properties which include: ease of donning without powder, increased tactile transmission, non-curling cuffs, and increased external friction for better gripping of instruments especially during a bloody operation, while the untreated surfaces of the glove are characterized by relatively high friction. The glove's cuff portion that fits over the surgeon's gown, because of its high friction will lock to the gown, thereby preventing loss of bacterial barrier, while treated or low friction surfaces of the glove retain their low friction characteristics, even while being extended during hand insertion.

Thus, the above described physical changes produced by the method of this invention give the glove's treated surfaces a reduced frictional coefficient that is retained even when and while the glove is extended by insertion of the surgeon's hand. It has been discovered that if the fluorine treatment of the glove is not carried out while the glove is extended by at least 10%, the desired physical changes do not occur. The reason is related to the fact that during glove extension a much larger surface area is exposed to the treating gas so that when the glove is again extended in use, it will continue to exhibit the desired physical properties.

While the invention has been described with respect to surgical gloves, it is not limited thereto and can be applied to other extensible hydrocarbon elastomer products in order to improve and modify their surface characteristics as above described.

What is claimed is:

1. A method of treating a surface of an extensible elastomeric hydrocarbon article, comprising:
   extending said surface by at least 10 percent, and
   treating the extended surface with a fluorinating gas mixture, including elemental fluorine.

2. The method of claim 1 wherein said gas mixture includes an inert gas.

3. The method of claim 2 wherein said inert gas is selected from the group consisting of nitrogen, helium, and argon.

4. A method of claim 2 wherein said inert gas is nitrogen.

5. The method of claim 4 including,
   prior to fluorinating said surface, exposing said surface to nitrogen to remove substantially all oxidizing agents therefrom.

6. The method of claim 5 wherein the volumetric ratio of said gas mixture is between 1 part of fluorine to 20 parts of nitrogen, and 5 parts of fluorine to 1 part nitrogen.

7. The method of claim 6 wherein the extension of said surface is produced by inflating said hydrocarbon article with said gas mixture.

8. The method of treating a desired surface of an extensible glove composed of an elastomeric hydrocarbon comprising:
   a. treating both sides of the surface with an inert gas consisting of nitrogen;
   b. extending the glove by at least 10 percent while treating the desired surface with a fluorinating gas mixture including fluorine;
   c. retreating the desired surface with nitrogen;
   d. cleaning the glove with a cleansing solution; and
   e. washing the glove to remove the cleansing solution.

9. The method of claim 8, wherein the glove is inflated in step (b) with said gas mixture to obtain said extension.

10. The method of claim 9, wherein said gas mixture includes nitrogen in a volumetric ratio between 1 part of fluorine to 20 parts of nitrogen, and five parts of fluorine to 1 part of nitrogen.

11. The method of claim 8, wherein the cleansing solution is 0.1 N. NaOH.

* * * * *